(12) United States Patent
O'Lenick, Jr.

(10) Patent No.: US 6,800,275 B1
(45) Date of Patent: Oct. 5, 2004

(54) CAPPED DIMER ACID POLYESTERS IN PERSONAL CARE APPLICATIONS

(75) Inventor: Anthony J. O'Lenick, Jr., Dacula, GA (US)

(73) Assignee: Zenitech LLC, Old Greenwich, CT (US)

(*) Notice: Subject to any disclaimer, the term of this patent is extended or adjusted under 35 U.S.C. 154(b) by 64 days.

(21) Appl. No.: 10/384,687

(22) Filed: Mar. 11, 2003

(51) Int. Cl.[7] .......................... A61K 7/06; C08G 63/54
(52) U.S. Cl. ................... 424/70.11; 528/295.3; 528/295.5; 528/301; 528/302
(58) Field of Search .................. 528/295.3, 295.5, 528/301; 424/70.11

(56) References Cited

U.S. PATENT DOCUMENTS 5,545,692 A    8/1996    Köhler

*Primary Examiner*—Samuel A. Acquah

(57) ABSTRACT

The present invention is directed to a series of polyester compounds made from the reaction of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group. These compounds are very well suited to the preparation of products for the personal care market.

18 Claims, No Drawings

CAPPED DIMER ACID POLYESTERS IN PERSONAL CARE APPLICATIONS

FIELD OF THE INVENTION

The present invention is directed to a series of polyester compounds made from the reaction of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group. These compounds are very well suited to the preparation of products for the personal care market.

BACKGROUND OF THE INVENTION

There has been a long felt need for water-soluble polymers that can be used in personal care applications. The products of choice are polymers, since the high molecular weight afforded by polymers results in less skin penetration. Products that do not penetrate the skin are desirable since they are less irritating to eye and skin, have a more persistent, more pleasant skin feel, and can be used to keep the desired actives on the surface of the skin. Keeping materials applied for topical benefits on the skin make the use of such formulations more effective in topical applications For many years there have been a number of polymers used in personal care applications based upon the free radical polymerization of monomers that contain reactive vinyl groups. Such products include acrylate esters and amides and vinyl pyrrolidone. These materials have the desired higher molecular weight but also contain unreacted vinyl monomer that is very undesirable in personal care applications.

The ability to make water-soluble or water dispersible polymers that do not contain unreacted monomer would be a key development. One such attempt is the preparation of urethanes. Urethanes however are the reaction product of isocynates, materials, which offer their own, set of problems when applied to the skin.

Polyesters are a class of compounds, which could offer some interest. However, almost all polyesters used in personal care applications contain no water-soluble groups. Typical of this are the oil soluble polymers of U.S. Pat. No. 5,545,692. This patent, issued August 1996 to Koehler et al, describes polyesters of dimer acid, but said esters are of hydrophobic diols. These products are used in plastic lubrication and are water insoluble. They lack the critical polyoxyalkylene groups and are not capped, as are the products of the current invention. The Koehler products are very different in structure, function and application than the polyesters of the present invention.

THE INVENTION

Objective of the Invention

One objective of the present invention to provide a series of polyester compounds based upon the reaction of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group. These compounds are very well suited to the preparation of products for the personal care market.

It is another object of the present invention to provide a process for conditioning skin with a series of polyester compounds based upon the reaction of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group. Said process encompasses the contacting the skin with an effective conditioning amount of said polyester polymer.

Still other objectives of the present, invention will become apparent as one reads and understands the present disclosure.

SUMMARY OF THE INVENTION

The present invention is drawn to a series of polyesters that arc well suited for use in personal care applications. They are the reaction product of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group.

The present invention is also drawn to a process for use of the series of polyesters made by the reaction product of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group.

The proper selection of the components results in the desired application attributes. The difunctional hydroxy compound has to be a polyoxyalkylene compound. This portion of the polyester provides not only crosslinking due to its difunctional nature, but as importantly provides a water-soluble group to the molecule. The difunctional carboxylic acid provides not only the crosslinking ability based upon its difunctional nature, but also provides the oil soluble portion of the molecule. The balance between the oil soluble and water-soluble groups in the polyester molecule account for the surface-active properties of the molecule. Too much water-soluble polyoxyalkylene group and the product lose surfactant properties and becomes merely a water-soluble polymer. Too much oil soluble difunctional carboxylic group and the product lose it surfactant properties and becomes merely a oil soluble polymer. Since the products used in personal care are aqueous, and require some oil loving properties to deposit on the skin, activity at the hair and skin or these products requires a balance between the oil soluble and water-soluble portions of the molecule. Finally, another critical component is the mono-functional carboxylic group, which caps the polymer and provides terminal oil soluble portion to the molecule. This lowers the critical micelle concentration and provides improved skin deposition.

DETAILED DESCRIPTION OF THE INVENTION

The compounds of the present invention conform to the following structure;

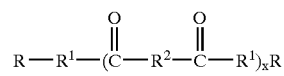

R is $R^3$—C(O)—O—
$R^1$ is

—O—$(CH_2$—$CH_2O)_n$—$(CH_2CH(CH_3)$—O$)_b$—$(CH_2$—$CH_2O)_c$—

$R^2$ is selected from the group consisting of:

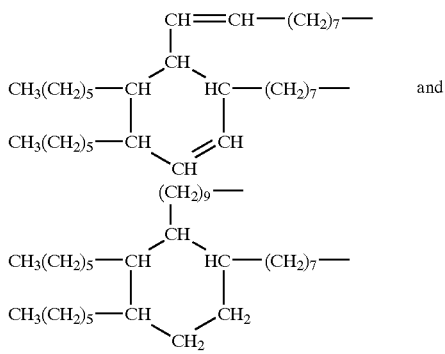

and $R^3$ is $CH_3-(CH_2)_n$;
n is an integer ranging from 6–38;
x is an integer ranging from 1 to 500.

The present invention is also directed to a process for conditioning skin, which comprises contacting the skin with an effective conditioning amount of a polyester conforming to the following structure;

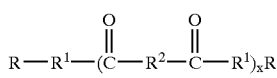

R is $R^3-C(O)-O-$
$R^1$ is

$R^2$ is selected from the group consisting of:

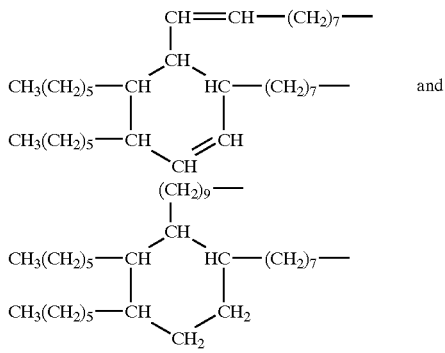

and $R^3$ is $CH_3-(CH_2)_n$;
n is an integer ranging from 6–38;
x is an integer ranging from 1 to 500.

Said conditioning concentration ranges from 0.1 to 20.0% by weight.

In a preferred embodiment of the process said conditioning concentration ranges from 1.0 to 20.0% by weight

Preferred Embodiments

In a preferred embodiment for the polyester n is 6.
In a preferred embodiment for the polyester n is 10.
In a preferred embodiment for the polyester n is 12.
In a preferred embodiment for the polyester n is 16.
In a preferred embodiment for the polyester n is 18.
In a preferred embodiment for the polyester n is 20.
In a preferred embodiment for the polyester n is 28.

In a preferred embodiment of the process said conditioning concentration ranges from 0.1 to 20.0% by weight.
In a preferred embodiment of the process said conditioning concentration ranges from 1.0 to 20.0% by weight
In a preferred embodiment of the process n is 6.
In a preferred embodiment of the process n is 10.
In a preferred embodiment of the process n is 12.
In a preferred embodiment of the process n is 16.
In a preferred embodiment of the process n is 18.
In a preferred embodiment of the process n is 20.
In a preferred embodiment of the process n is 28.

RAW MATERIAL EXAMPLES (A) Difunctional Hydroxy Compounds

The difunctional hydroxy compounds of the present invention are polyoxyalkylene compounds made by the reaction of ethylene oxide and propylene oxide. They are sold under the trade name Pluronic™ by BASF. The structures of the compounds listed below were determined by analysis and are not dependant upon any trade name.

| Example | a | b | c |
| --- | --- | --- | --- |
| 1 | 5 | 0 | 0 |
| 2 | 9 | 0 | 0 |
| 3 | 10 | 0 | 0 |
| 4 | 20 | 0 | 20 |
| 5 | 0 | 5 | 0 |
| 6 | 0 | 10 | 0 |
| 7 | 0 | 20 | 0 |
| 8 | 5 | 5 | 5 |
| 9 | 10 | 10 | 10 |
| 10 | 5 | 20 | 10 |
| 11 | 20 | 20 | 20 |
| 12 | 10 | 5 | 10 |

(B) Difunctional Carboxylic Acids

Example 13

Dimer Acid

Dimer acid is an item of commerce available from a variety of sources including Cognis. It is the reaction product of linoleic acid and oleic acid. It conforms to the following structure;

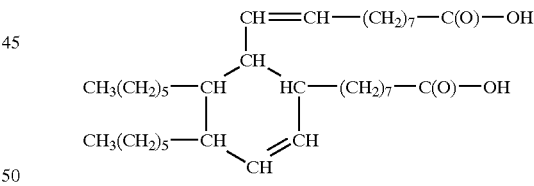

Example 14

Hydrogenated Dimer Acid

Hydrogenated dimer acid is an item of commerce available from a variety of sources including Cognis. It is the reaction product of dimer acid and hydrogen. It conforms to the following structure;

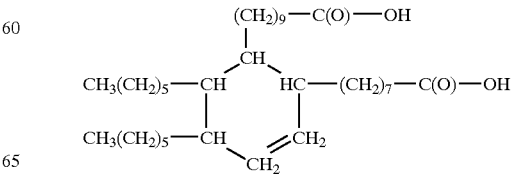

(C) Capping Carboxylic Acids

The capping carboxylic acids are fatty acids available from a variety of source including Cognis.

| Example | n | Common Name |
|---|---|---|
| 15 | 6 | carpylic acid |
| 16 | 10 | lauric acid |
| 17 | 12 | myristic acid |
| 18 | 16 | stearic acid |
| 19 | 18 | arachadonic acid |
| 20 | 20 | behenic acid |
| 21 | 28 | myricic acid |

It should be clearly understood that the use of the term "acid" when used as a raw material in this section would also include methyl ester and triglyceride. All three classes are functional. When the acid is reacted water is produced, when the methyl ester is used methanol is produced, and when the triglyceride is used glycerin is produced.

Polyester General Process

The esterification reaction is carried out by reacting the specified amount of the specified raw materials at a temperature of between 180 and 220° C. Water is removed during the reaction. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure

In a suitable vessel equipped with agitation, heat and an ability to distill off water is added the specified amount of the specified of difunctional hydroxy compound (example 1–12) is added the specified amount of the specified dimer acid (example 13–14). Next add 0.1% stannous oxylate based upon the total weight of the batch after all ingredients have been charged, under agitation. The temperature of the mass is raised to 180–200° C. and water is stripped off as formed. The temperature is held 4–8 hours or until acid value is vanishingly small. Next add the specified amount of the specified capping acid (example 15–21). Hold at 180–200° C. for another 4–8 hours. The acid value and hydroxyl value drop to vanishingly small values.

Applications Examples

The compounds of the present invention are easily put into water, either as self-dispersing materials or as emulsions with additional surfactant. The fact that they contain the three functional groups, and have water-soluble polyoxyalkylene groups and oil soluble capping groups and dimer acid, results in highly lubricious materials that are substantive to the skin.

The compounds of the present invention provide conditioning effects to the skin, re-hydrating it while at the same time minimizing trans epidermal water loss.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A polyester compound conforming to the following structure;

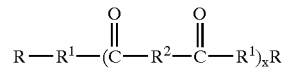

R is $R^3$—C(O)—O—

$R^1$ is

—O—(CH$_2$—CH$_2$O)$_a$—(CH$_2$CH(CH$_3$)—O)$_b$—(CH$_2$—CH$_2$O)$_c$—

$R^2$ is selected from the group consisting of:

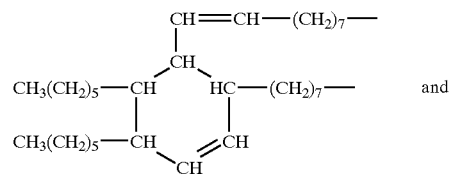

and

| | x | Dihydroxy | | Dicid | | Capping | |
|---|---|---|---|---|---|---|---|
| Example | value | Example | Grams | Example | Grams | Example | Grams |
| 22 | 3 | 1 | 302.0 | 13 | 580.0 | 15 | 118.0 |
| 23 | 5 | 2 | 419.0 | 14 | 501.0 | 16 | 80.0 |
| 24 | 1 | 3 | 450.0 | 13 | 288.0 | 17 | 262.0 |
| 25 | 10 | 4 | 756.0 | 14 | 222.0 | 18 | 22.0 |
| 26 | 30 | 5 | 343.0 | 13 | 634.0 | 19 | 23.0 |
| 27 | 51 | 6 | 507.0 | 14 | 478.0 | 20 | 15.0 |
| 28 | 5 | 7 | 642.0 | 13 | 256.0 | 21 | 102.0 |
| 29 | 20 | 8 | 569.0 | 14 | 419.0 | 15 | 13.0 |
| 30 | 9 | 9 | 727.0 | 13 | 251.0 | 16 | 23.0 |
| 31 | 96 | 10 | 764.0 | 14 | 234.0 | 17 | 2.0 |
| 32 | 27 | 11 | 880.0 | 13 | 116.0 | 18 | 4.0 |
| 33 | 500 | 12 | 674.0 | 14 | 325.0 | 19 | 1.0 |

-continued

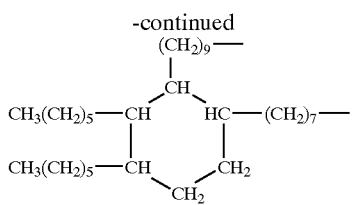

$R^3$ is $CH_3-(CH_2)_n$;
n is an integer ranging from 6–38;
x is an integer ranging from 1 to 500.

2. A polyester compound of claim 1 wherein n is 6.
3. A polyester compound of claim 1 wherein n is 10.
4. A polyester compound of claim 1 wherein n is 12.
5. A polyester compound of claim 1 wherein n is 16.
6. A polyester compound of claim 1 wherein n is 18.
7. A polyester compound of claim 1 wherein n is 20.
8. A polyester compound of claim 1 wherein n is 28.
9. The present invention is also directed to a process for conditioning skin, which comprises contacting the skin with an effective conditioning amount of a polyester conforming to the following structure;

$$R-R^1-(\overset{O}{\underset{\|}{C}}-R^2-\overset{O}{\underset{\|}{C}}-R^1)_x R$$

R is $R^3-C(O)-O-$
$R^1$ is

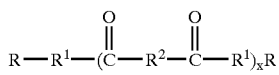

$R^2$ is selected from the group consisting of:

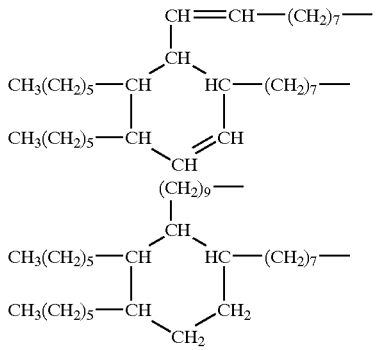

and $R^3$ is $CH_3-(CH_2)_n$;
n is an integer ranging from 6–38;
x is an integer ranging from 1 to 500.

10. A process of claim 9 wherein said conditioning concentration ranges from 0.1 to 20.0% by weight.
11. A process of claim 9 wherein said conditioning concentration ranges from 1.0 to 20.0% by weight.
12. A process of claim 9 wherein n is 6.
13. A process compound of claim 9 wherein n is 10.
14. A process compound of claim 9 wherein n is 12.
15. A process compound of claim 9 wherein n is 16.
16. A process compound of claim 9 wherein n is 18.
17. A process compound of claim 9 wherein n is 20.
18. A process compound of claim 9 wherein n is 28.

* * * * *